US00PP24686P2

(12) United States Plant Patent
van den Hoogen

(10) Patent No.: US PP24,686 P2
(45) Date of Patent: Jul. 22, 2014

(54) ***CAMPANULA* PLANT NAMED 'ALLGENTIW'**

(50) Latin Name: *Campanula glomerata*
Varietal Denomination: Allgentiw

(71) Applicant: Wilhelmus T. J. van den Hoogen, Cuijk (NL)

(72) Inventor: Wilhelmus T. J. van den Hoogen, Cuijk (NL)

(73) Assignee: All Plants Holding B.V., Cuijk (NL)

( * ) Notice: Subject to any disclaimer, the term of this patent is extended or adjusted under 35 U.S.C. 154(b) by 39 days.

(21) Appl. No.: 13/694,022

(22) Filed: Oct. 20, 2012

(51) Int. Cl.
*A01H 5/00* (2006.01)

(52) U.S. Cl.
USPC ..... Plt./414

(58) Field of Classification Search
USPC ..... Plt./414
See application file for complete search history.

*Primary Examiner* — Kent L Bell
(74) *Attorney, Agent, or Firm* — C. A. Whealy

(57) ABSTRACT

A new and distinct cultivar of *Campanula* plant named 'Allgentiw' characterized by its compact and broadly upright plant habit; freely basal branching habit; early, freely and uniformly flowering habit; white-colored campanulate-shaped flowers; and good garden performance.

3 Drawing Sheets

Botanical designation: *Campanula glomerata.*
Cultivar denomination: 'ALLGENTIW'.

CROSS-REFERENCED TO CLOSELY-RELATED APPLICATIONS

Title: *Campanula* Plant Named 'ALLGENTIBL'
Applicant: Wilhelmus T. J. van den Hoogen
Filed: Concurrently with this application U.S. Plant patent application Ser. No. 13/694,021.

BACKGROUND OF THE INVENTION

The present invention relates to a new and distinct cultivar of *Campanula* plant, botanically known as *Campanula glomerata* and hereinafter referred to by the name 'Allgentiw'.

The new *Campanula* is a product of a planned breeding program conducted by the Inventor in Cuijk, The Netherlands. The objective of the breeding program is to create new compact and freely flowering *Campanula* plants with good garden performance.

The new *Campanula* plant originated from an open-pollination in Cuijk, The Netherlands in June, 2006 of a proprietary selection of *Campanula glomerata* identified as code number CamZ05-3, not patented, as the female, or seed, parent with an unknown selection of *Campanula glomerata* as the male, or pollen, parent. The new *Campanula* was discovered and selected by the Inventor as a single flowering plant from within the progeny of the stated open-pollination grown in a controlled outdoor nursery in Cuijk, The Netherlands in June, 2008.

Asexual reproduction of the new *Campanula* plant by tissue culture in The Netherlands, since May, 2009 has shown that the unique features of this new *Campanula* plant are stable and reproduced true to type in successive generations.

SUMMARY OF THE INVENTION

Plants of the new *Campanula* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Allgentiw'. These characteristics in combination distinguish 'Allgentiw' as a new and distinct *Campanula* plant:

1. Compact and broadly upright plant habit.
2. Freely basal branching habit.
3. Early, freely and uniformly flowering habit.
4. White-colored campanulate-shaped flowers.
5. Good garden performance.

Plants of the new *Campanula* differ from plants of the female parent selection in the following characteristics:

1. Plants of the new *Campanula* are more compact than plants of the female parent selection.
2. Plants of the new *Campanula* flower earlier than plants of the female parent selection.
3. Plants of the new *Campanula* and the female parent selection differ in flower color as plants of the female parent selection have purple violet-colored flowers.

Plants of the new *Campanula* can be compared to plants of *Campanula glomerata* 'Allgentibl', disclosed in U.S. Plant patent application 13/694,021 filed concurrently. Plants of the new *Campanula* differ primarily from plants of 'Allgentibl' in flower color as plants of 'Allgentiw' have dark purple violet-colored flowers.

Plants of the new *Campanula* can be compared to plants of *Campanula glomerata* 'Emerald', disclosed in U.S. Plant Pat. No. 18,343. In side-by-side comparisons conducted in Cuijk, The Netherlands, plants of the new *Campanula* differed primarily from plants of 'Emerald' in the following characteristics:

1. Plants of the new *Campanula* were more compact than plants of 'Emerald'.
2. Plants of the new *Campanula* flowered more uniformly than plants of 'Emerald'.

3. Plants of the new *Campanula* and 'Emerald' differed in flower color as plants of 'Emerald' had light purple-colored flowers.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet is a side perspective view of a typical flowering plant of 'Allgentiw'.

The photograph on the second sheet is a close-up view of a typical flowering plant of 'Allgentiw'.

The photograph on the third sheet is a close-up view of the upper surface of a typical leaf of 'Allgentiw'.

DETAILED BOTANICAL DESCRIPTION

Plants used for the aforementioned photographs and following description were grown during the early summer in an outdoor nursery in Cuijk, The Netherlands and under cultural practices which closely approximate commercial production conditions. Plants used for the photographs were grown in 13-cm containers and plants used for the description were grown in ground beds. During the production of the plants, day temperatures ranged from 15° C. to 28° C. and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Campanula glomerata* 'Allgentiw'.

Parentage:

*Female parent*.—Proprietary selection of *Campanula glomerata* identified as code number CamZ05-3, not patented.

*Male parent*.—Unknown selection of *Campanula glomerata*, not patented.

Propagation:

*Type*.—By tissue culture.

*Time to initiate roots, summer*.—About 20 days at 6° C. to 28° C.

*Time to initiate roots, winter*.—About 25 days at 6° C. to 28° C.

*Time to produce a rooted young plant, summer*.—About 30 days at 6° C. to 28° C.

*Time to produce a rooted young plant, winter*.—About 35 days at 6° C. to 28° C.

*Root description*.—Fine, fibrous; white in color.

*Rooting habit*.—Moderately freely branching; medium density.

Plant description:

*Plant and growth habit*.—Herbaceous perennial; compact and broadly upright plant habit; overall shape, roughly globular; freely basal branching habit with about 14 basal branches developing per plant; moderately vigorous growth habit; campanulate flowers arranged in compound racemes positioned above and beyond the foliar plant.

*Plant height*.—About 29.9 cm.

*Plant width*.—About 42 cm.

*Basal branch description*.—Aspect: About 15° from vertical. Length: About 21.1 cm. Diameter: About 4 mm. Internode length: About 3.4 cm. Strength: Strong. Texture: Moderately pubescent. Color: Close to 144B to 144C.

Foliage description:

*Arrangement*.—Alternate, simple.

*Length*.—About 10.2 cm.

*Width*.—About 4.8 cm.

*Shape*.—Ovate.

*Apex*.—Acute to broadly acute.

*Base*.—Basal leaves, cordate; upper leaves, obtuse.

*Margin*.—Irregularly and finely serrate.

*Texture, upper surface*.—Sparsely pubescent; rough; slightly rugose.

*Texture, lower surface*.—Moderately pubescent; rough; slightly rugose.

*Venation pattern*.—Pinnate.

*Color*.—Developing leaves, upper surface: Close to N137B to N137C; towards the base, close to 143C. Developing leaves, lower surface: Close to 137C. Fully expanded leaves, upper surface: Close to N137B; venation, 138B to 138C. Fully expanded leaves, lower surface: Close to 137C; venation, close to between 143C and 144A.

*Petioles*.—Basal leaves, petiolate; upper leaves, sessile. Length: About 12.8 cm. Diameter: About 2.5 mm. Texture, upper and lower surfaces: Sparsely pubescent. Color, upper and lower surfaces: Close to 144A to 144B.

Flower description:

*Flower arrangement and shape*.—Single campanulate star-shaped flowers arranged in axillary and terminal racemes; flowers face mostly upright to slightly outwardly; freely flowering habit with about twelve flowers developing per terminal inflorescence and about seven flowers developing per axillary inflorescence.

*Natural flowering season*.—Early and uniformly flowering habit; flowering continuous from late May to early August in The Netherlands.

*Flower longevity on the plant*.—About ten days; flowers persistent.

*Fragrance*.—None detected.

*Inflorescence height*.—About 3.6 cm.

*Inflorescence diameter*.—About 5.9 cm.

*Flower buds*.—Length: About 1.8 cm. Diameter: About 7 mm. Shape: Narrowly oblong. Color: Petals, between 155C and 157D and towards the apex, close to 145D; sepals, close to 143C and towards the base, close to 145A to 145B.

*Flowers*.—Diameter: About 2.5 cm. Depth (height): About 3 cm.

*Petals*.—Arrangement: Five in a single whorl; petals fused. Length: About 3 cm. Width, base of free part of the petal: About 8 mm. Shape: Narrowly oblong. Apex: Acute. Margin: Entire. Texture, upper surface: Sparsely pubescent. Texture, lower surface: Smooth, glabrous. Color: When opening, upper and lower surfaces: Close to NN155D. Fully opened, upper and lower surfaces: Close to NN155D.

*Sepals*.—Arrangement: Five in a single campanulate whorl; fused. Length: About 1.2 cm. Width, base of free part of the sepal: About 4 mm. Shape: Lanceolate. Apex: Narrowly acute. Margin: Entire. Texture, upper surface: Smooth, glabrous; pubescence along the margins. Texture, lower surface: Moderately pubescent. Color, immature, upper and lower surfaces: Close to 143C; towards the base, close to 145A to 145B. Color, mature, upper and lower surfaces: Close to 143A; towards the base, close to 145B.

*Pedicels*.—Length: About 2 mm. Diameter: About 1.5 mm. Aspect: Upright. Strength: Strong. Texture: Slightly pubescent. Color: Close to 145B.

*Reproductive organs*.—Stamens: Quantity per flower: Five. Filament length: About 3 mm. Filament width: About 1.5 mm, flattened. Filament color: Close to NN155C. Anther length: About 6 mm. Anther shape: Narrowly lanceolate. Anther color: Close to 8B to 8C. Pollen amount: Scarce. Pollen color: Close to 8D. Pistils: Quantity per flower: One. Pistil length: About 1.8 cm. Stigma shape: Narrowly lanceolate; decurrent. Stigma color: Close to 157A. Style length: About 1.4 cm. Style color: Close to 157D; towards the base, close to NN155C to NN155D. Ovary color: Close to 145C to 145D.

*Seeds and fruits*.—Seed and fruit production have not been observed on plants of the new *Campanula*.

Disease & pest resistance: Plants of the new *Campanula* have not been observed to be resistant to pathogens and pests common to *Campanula* plants.

Garden performance: Plants of the new *Campanula* have exhibited good tolerance to rain and wind, are hardy to USDA Hardiness Zone 3 and have been observed to tolerate high temperatures of about 35° C.

It is claimed:

1. A new and distinct *Campanula* plant named 'Allgentiw' as illustrated and described.

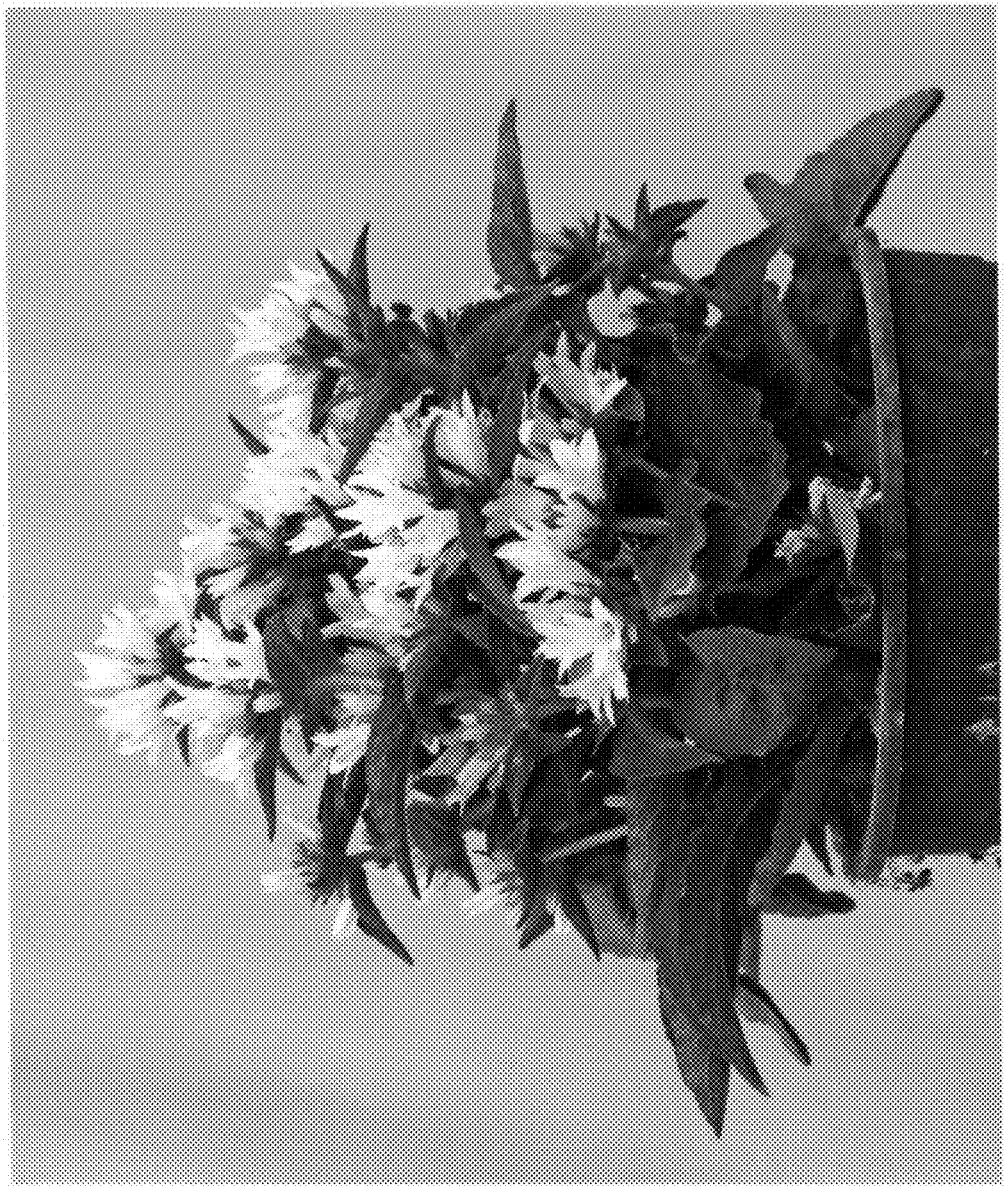

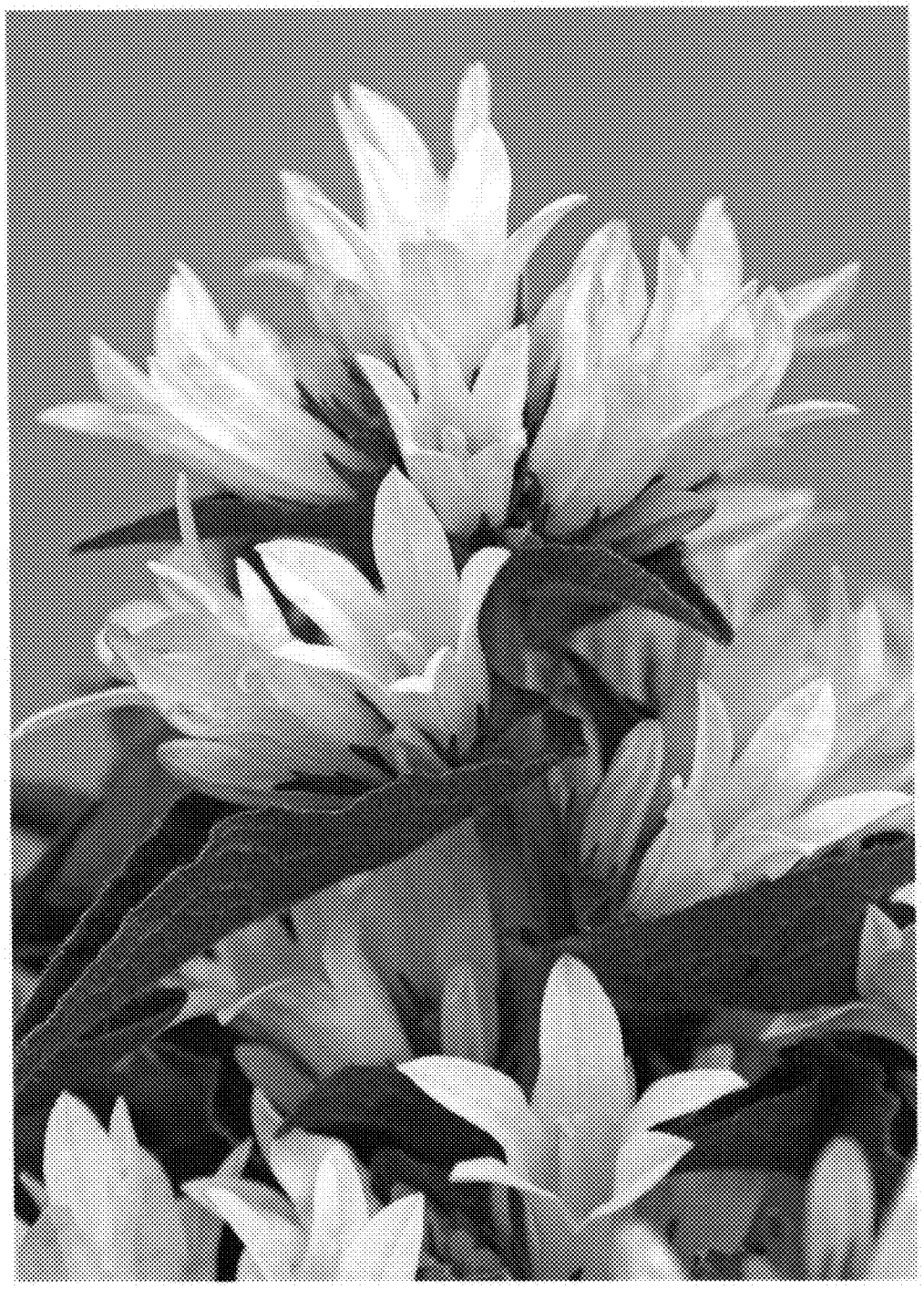

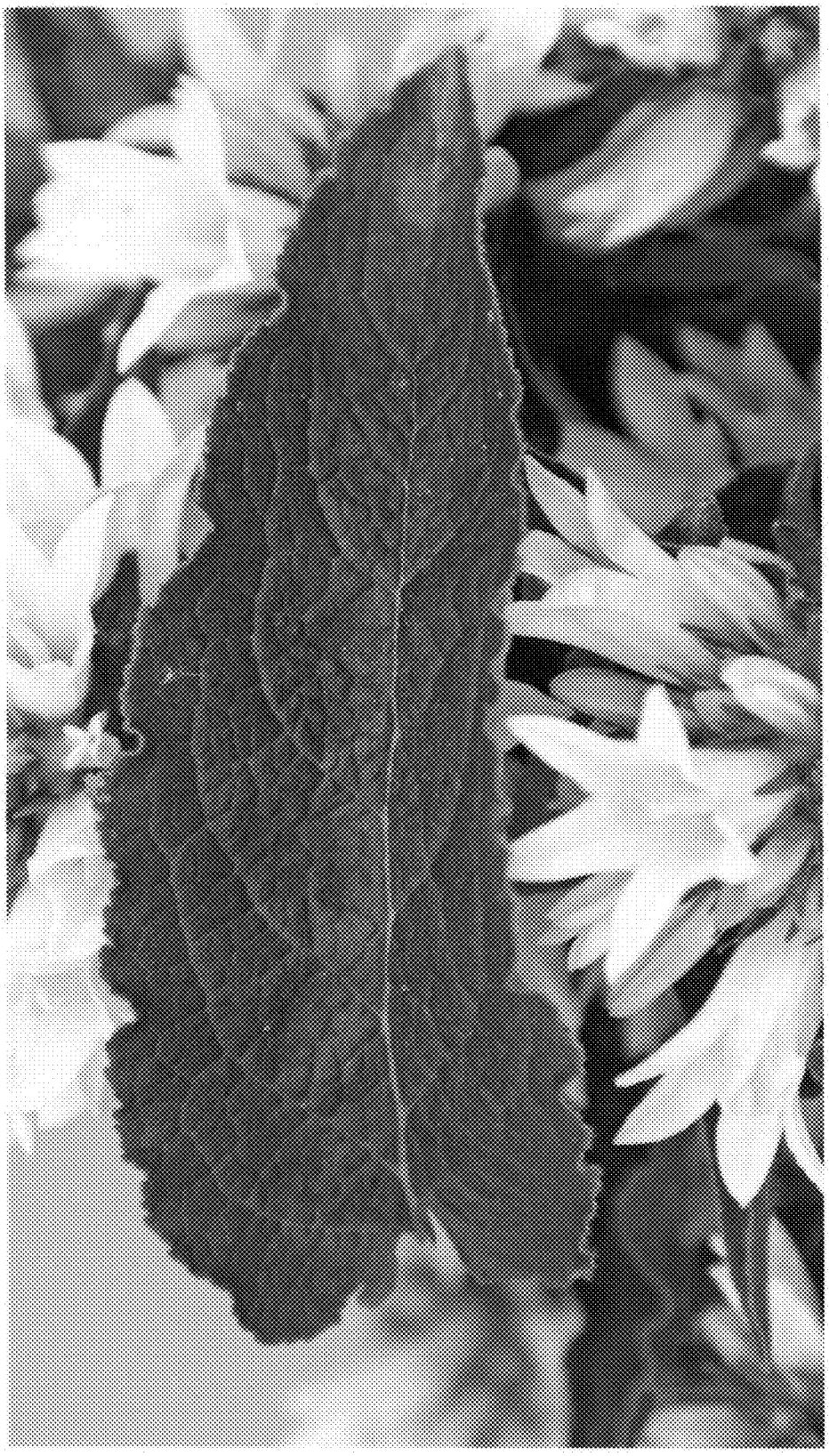

* * * * *